US010213625B2

(12) United States Patent
Goebel

(10) Patent No.: US 10,213,625 B2
(45) Date of Patent: *Feb. 26, 2019

(54) PROTON IRRADIATION USING SPOT SCANNING

(71) Applicant: Varian Medical Systems Particle Therapy GmbH, Troisdorf (DE)

(72) Inventor: Holger Goebel, Nuembrecht (DE)

(73) Assignee: Varian Medical Systems Particle Therapy GMBH, Troisdorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/402,080

(22) Filed: Jan. 9, 2017

(65) Prior Publication Data

US 2017/0189723 A1    Jul. 6, 2017

Related U.S. Application Data

(63) Continuation of application No. 13/043,208, filed on Mar. 8, 2011, now Pat. No. 9,539,442.

(51) Int. Cl.
- *A61N 5/10* (2006.01)
- *H01J 47/02* (2006.01)
- *H05H 7/04* (2006.01)
- *H05H 13/00* (2006.01)
- *H05H 7/00* (2006.01)

(52) U.S. Cl.
CPC ......... *A61N 5/1071* (2013.01); *A61N 5/1067* (2013.01); *A61N 5/1077* (2013.01); *H01J 47/02* (2013.01); *H05H 7/001* (2013.01); *H05H 7/04* (2013.01); *H05H 13/005* (2013.01); *A61N 2005/1087* (2013.01); *H05H 2007/004* (2013.01)

(58) Field of Classification Search
CPC .. A61N 5/1043; A61N 5/1071; A61N 5/1079; A61N 2005/1087; A61N 5/1075; H01J 47/02
USPC .......................................................... 250/375
See application file for complete search history.

(56) References Cited

U.S. PATENT DOCUMENTS

| 5,012,111 A * | 4/1991 | Ueda ........................ A61N 5/10 250/492.1 |
| 6,677,597 B1 | 1/2004 | Haberer et al. |
| 7,301,162 B2 | 11/2007 | Matsuda et al. |
| (Continued) | | |

FOREIGN PATENT DOCUMENTS

| EP | 1 656 966 | 5/2006 |
| WO | 2008003527 | 1/2008 |

*Primary Examiner* — David Porta
*Assistant Examiner* — Gisselle Gutierrez

(57) ABSTRACT

In one embodiment of the invention, a method for irradiating a target is disclosed. A proton beam is generated using a cyclotron. A first information is provided to an energy selection system. An energy level for the protons is selected using an energy selection system based on the first information. The first information comprises a depth of said target. The proton beam is routed from the cyclotron through a beam transfer line to a scanning system. A second information is provided to the scanning system. The second information comprises a pair of transversal coordinates. The proton beam is guided to a location on the target determined by the second information using a magnet structure. The target is irradiated with the protons.

20 Claims, 6 Drawing Sheets

(56) References Cited

U.S. PATENT DOCUMENTS

| | | | |
|---|---|---|---|
| 2003/0015666 A1* | 1/2003 | Morgan | G21G 1/10 250/398 |
| 2005/0139787 A1* | 6/2005 | Chiba | A61N 5/10 250/492.3 |
| 2006/0033042 A1* | 2/2006 | Groezinger | A61N 5/1043 250/492.1 |
| 2006/0102856 A1* | 5/2006 | Matsuda | A61N 5/1043 250/492.22 |
| 2007/0108922 A1 | 5/2007 | Amaldi | |
| 2008/0234531 A1 | 9/2008 | Welch et al. | |
| 2009/0168960 A1* | 7/2009 | Jongen | A61N 5/1049 378/65 |
| 2009/0236545 A1 | 9/2009 | Timmer | |
| 2009/0309520 A1 | 12/2009 | Balakin | |
| 2010/0012859 A1 | 1/2010 | Claereboudt | |
| 2011/0049372 A1 | 3/2011 | Iseki et al. | |

* cited by examiner

PROTON IRRADIATION USING SPOT SCANNING

CLAIM OF PRIORITY

This application is a continuation of and claims priority to U.S. patent application Ser. No. 13/043,208 filed Mar. 8, 2011 and entitled "PROTON IRRADIATION USING SPOT SCANNING," which is herein incorporated by reference in its entirety.

FIELD OF THE INVENTION

This invention relates generally to proton beam generation and manipulation technology, and more specifically to medicinal processes utilizing proton irradiation.

BACKGROUND OF THE INVENTION

Among the more invidious aspects of cancer is how it hijacks an organism's own cells and propagates rapidly while remaining intermingled with healthy tissue. For this reason, scientists and engineers have found it difficult to develop a cancer treatment that can distinguish between healthy tissue that should be left alone and cancerous cells that must be destroyed. For example, radiation therapy is used against cancer because the rapidly growing cancer cells divide faster and are therefore more susceptible to radiation. However, all living cells in a patient's body are continuously dividing so the radiation also causes harm to healthy tissue and in turn causes the well known debilitating side effects of radiation therapy. Given that this aspect of cancer is a chief contributor to its status as a worldwide epidemic, a broad tranche of cancer research is directed to the production of treatments that can be more accurately targeted to the cancer itself.

The use of accelerated protons to bombard cancer cells was pioneered in the middle of the 20th century by nuclear scientists working in particle accelerator laboratories. Since then the field of proton therapy has developed into a successful weapon in the medical profession's arsenal against cancer. The general concept of proton therapy involves bombarding a tumor using a beam of accelerated protons. As with other types of radiotherapy the protons are a form of ionizing radiation that more strongly effect cells that are rapidly dividing. In addition, the beam can be focused directly on a tumor and will therefore cause minimal harm to the surrounding healthy tissue. In this sense proton therapy is similar to other forms of beam directed radiation treatments such as x-ray radiation therapy. However, proton therapy combined with the spot scanning carries the additional and unique benefit of better three dimensional dose conformity than known therapy methods on the market. In most cases no patient specific collimators are needed.

As seen in FIG. 1, proton therapy is superior to x-ray radiation therapy in terms of its ability to prevent damage to surrounding healthy tissue. X-axis 101 shows the depth of the particles and y-axis 102 shows the proportional radiation dose delivered at a given depth. The proportional dose of radiation delivered by the photons in x-ray radiation therapy is shown by photon dose distribution line 103. Photon dose distribution line 103 peaks at a low depth and then gradually tapers out. To increase the radiation delivered at a desired depth, damage to the healthy tissue above the tumor must be proportionally increased. In comparison, proton dose distribution line 104 minimizes the radiation delivered before and after the target and delivers nearly all of its energy in a given window of depth. The peak of the proton dose distribution line is called the Bragg peak.

The acceleration of protons requires the use of a particle accelerator. Two common types of particle accelerators are cyclotrons and synchrotrons. Both types of accelerators depend on the interplay of magnetic and electric fields. Synchrotrons accelerate particles through a path having a constant radius and adjust the magnetic and electric fields as the particles gain momentum. Cyclotrons accelerate charged particles using a high frequency alternating voltage. A perpendicular magnetic field causes the particles to move in an expanding spiral wherein they re-encounter the accelerating voltage. When the particles reach a predetermined radius they are guided out of the cyclotron in an accelerated state.

SUMMARY OF INVENTION

In one embodiment of the invention, a method for irradiating a target is provided. In one step a proton beam is generated using a cyclotron. In another step a first information is provided to an energy selection system. In another step an energy level for the protons is selected using an energy selection system based on the first information. The first information comprises a depth of the target. In another step the proton beam is routed from the cyclotron through a beam transfer line to a scanning system. In another step a second information is provided to the scanning system. The second information comprises a pair of transversal coordinates. In another step the proton beam is guided to a location on the target determined by the second information using a magnet structure. In another step the target is irradiated with the protons with the number of protons or with protons up to a given number with corresponds to the number of protons determined by a third information.

DETAILED DESCRIPTION OF THE PREFERRED EMBODIMENTS

Figure 1:
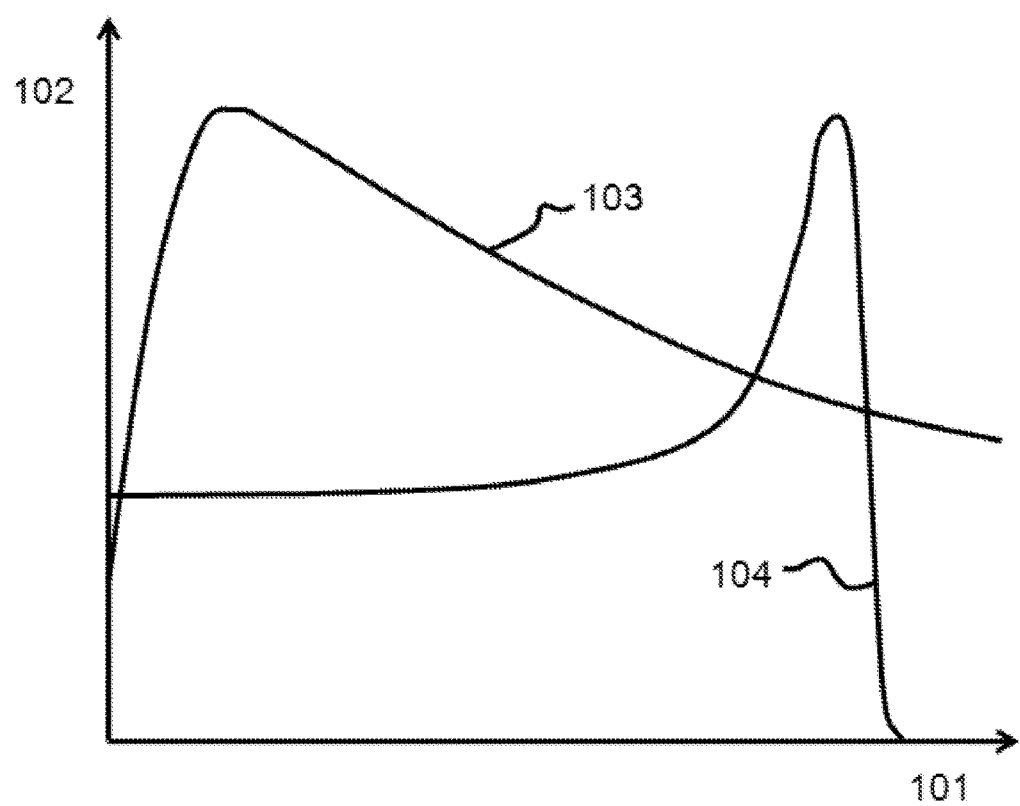
FIG. 1 illustrates the dose distribution lines of photons and protons as used in the prior art.

Reference will now be made in detail to embodiments of the present invention, examples of which are illustrated in the accompanying drawings. While the invention will be described in conjunction with these embodiments, it will be understood that they are not intended to limit the invention to these embodiments. On the contrary, the invention is intended to cover alternatives, modifications and equivalents, which may be include within the spirit and scope of the invention as defined by the appended claims. Furthermore, in the following detailed description of embodiments of the present invention, numerous specific details are set forth in order to provide a thorough understanding of the present invention. However, it will be recognized by one of ordinary skill in the art that the present invention may be practiced without these specific details. In other instances, well-known methods, procedures, components, and circuits have not been described in detail as not to unnecessarily obscure aspects of the embodiments of the present invention.

The prime advantage of proton radiation therapy is the mitigation of any commensurate harm to healthy tissue that accompanies the delivery of ionizing radiation to a targeted tumor. Other methods of radiation delivery can cause significant harm to healthy tissue and deleterious side effects. Proton radiation therapy does however share one of the main drawbacks of other therapy involving accelerated particles in that the associated equipment is extremely expensive. The capital investment necessary to create a functioning proton therapy facility can exceed one-hundred-million dollars.

Embodiments of the present invention build upon the advantages of proton radiation therapy. In specific embodiments of the invention, the radiation dose of a proton beam is more particularly targeted to cancer cells. This is achieved in certain embodiments through the use of a spot scanning method using three dimensional targeting. In specific embodiments of the invention, the three dimensional targeting is updated in real time as a particular round of treatment is conducted. Real time updating of the targeted proton beam helps to adjust for changes in the location of the target. For example, when the target is a tumor the target will move due to the treatment itself and also the movement of the patient's body. Real time updating also helps to compensate for inaccuracies in the delivery system that cause the radiation to be applied to an area different from the one desired. Finally, real time updating can keep track of the actual dose that has been administered and alter the course of treatment as needed. Specific embodiments of the invention enhance the benefit of proton beam radiation therapy by applying a more focused dose of radiation to a target and by adjusting this application to assure that it is most efficiently applied to the target.

Embodiments of the present invention erode the disadvantages associated with particle acceleration therapy. In specific embodiments of the invention, a single particle accelerator is used to provide a proton beam to several treatment rooms. This drastically reduces per patient costs associated with a radiation therapy facility having one accelerator per treatment room or having a single treatment room that must be shared by multiple patients. In specific embodiments of the invention, the accelerated protons are routed through a beam transfer line using adjustable magnetic fields that provide increased flexibility in how and where the protons are finally delivered.

Figure 2:
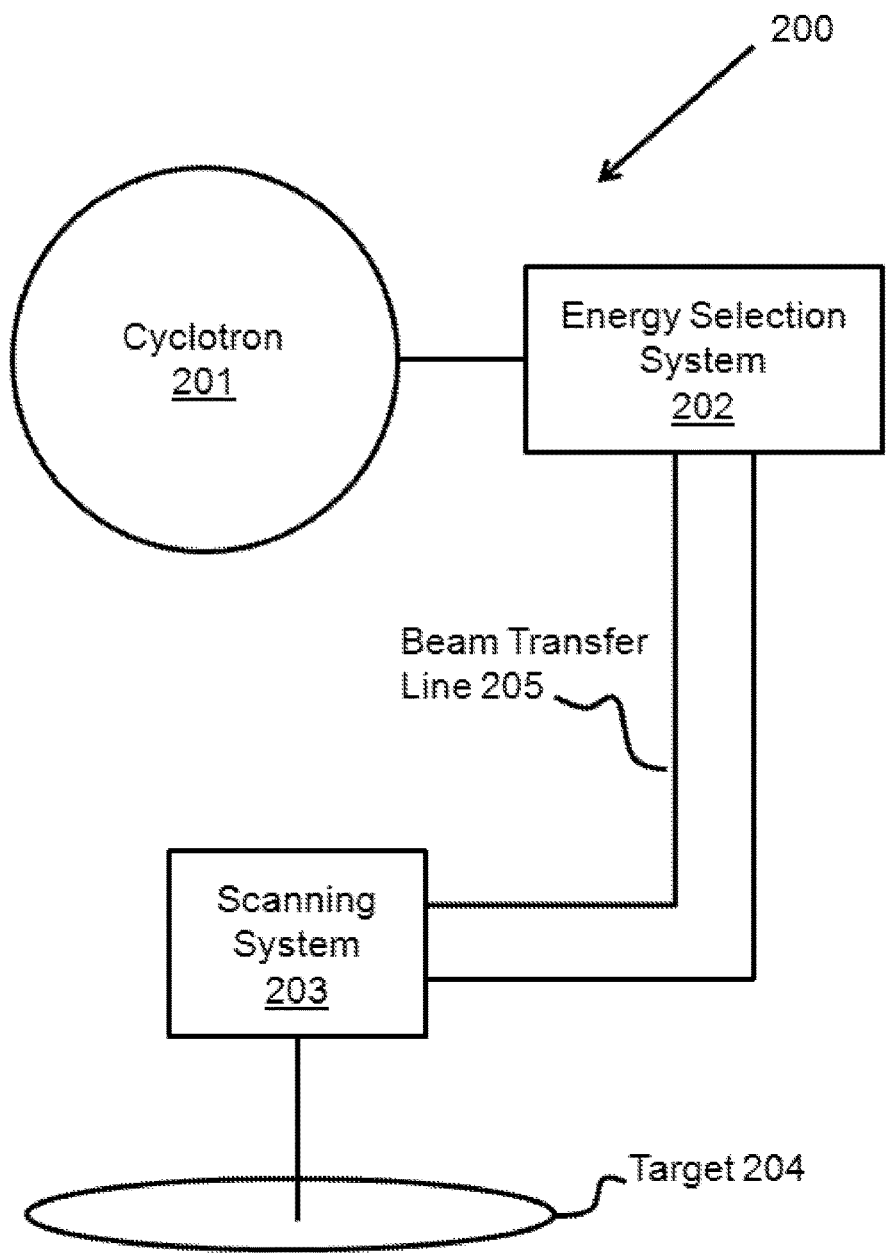
FIG. 2 illustrates a block diagram of an apparatus for irradiating a target that is in accordance with the present invention.

A specific embodiment of the invention can be described with reference to FIG. 2. FIG. 2 illustrates an apparatus and system for irradiating a target. System 200 comprises cyclotron 201 which is configured to generate a proton beam. In specific embodiments of the invention cyclotron 201 is a superconducting cyclotron. The energy level for protons in the proton beam is selected using energy selection system 202. Energy selection system 202 can set an energy level continuously up to the fixed energy of the accelerated protons by the cyclotron. In specific embodiments of the invention, this energy selection is based on a first information which may be deterministic information provided by the treatment plan or provided by a system with derives this information. Scanning system 203 guides the proton beam to a location on target 204 using a magnet structure. In specific embodiments of the invention, scanning system 203 guides the proton beam according to a second information which may be deterministic information provided by the treatment plan or provided by a system with derives this information. In specific embodiments of the invention, system 200 is capable of three dimensional spot scanning because the energy level for protons in the proton beam is selected based on a depth of the target and the transversal coordinates of the beam can be adjusted by the scanning system. Adjusting the energy level of the beam allows control of the depth at which the Bragg Peaks of the accelerated protons are located. The increased flexibility made available through three dimensional spot scanning greatly improves the precision of the dose delivered to a patient so as to maximize dose delivery to a tumor and minimize damage to healthy tissue.

Spot scanning of target 204 can be conducted in accordance with several variant methodologies. In specific embodiments of the invention, target 204 is a tumor and the location to which the proton beam is guided is selected based on patient location data regarding a specific patient that is undergoing proton radiation therapy. The patient location data may include information about the location of certain anatomical structures within a patient and may also include the location of a tumor within the patient's body. Spot scanning of target 204 can be conducted in multiple sessions with the same or variant spot scanning patterns. In specific embodiments of the invention, scanning system 203 and energy selection system 202 will both alter their values during a given application of protons so that three dimensional spot scanning can be achieved. In specific embodiments of the invention, the intensity of the proton beam will be altered along with the energy of the proton beam and/or with the transversal coordinates to more accurately control the delivery of radiation to the target at a specific location. In specific embodiments of the invention, scanning system 203 adjusts the location of beam delivery during an application while the energy level remains constant so that the protons are applied in a transversally varying manner while the depth of the Bragg Peak remains constant. In order to have a medically significant effect on tumors a single session of proton radiation therapy does not have to be great in length. A single irradiation session can involve the irradiation of 400 different spots in a 100 $cm^2$ space in less than one second.

Figure 3:
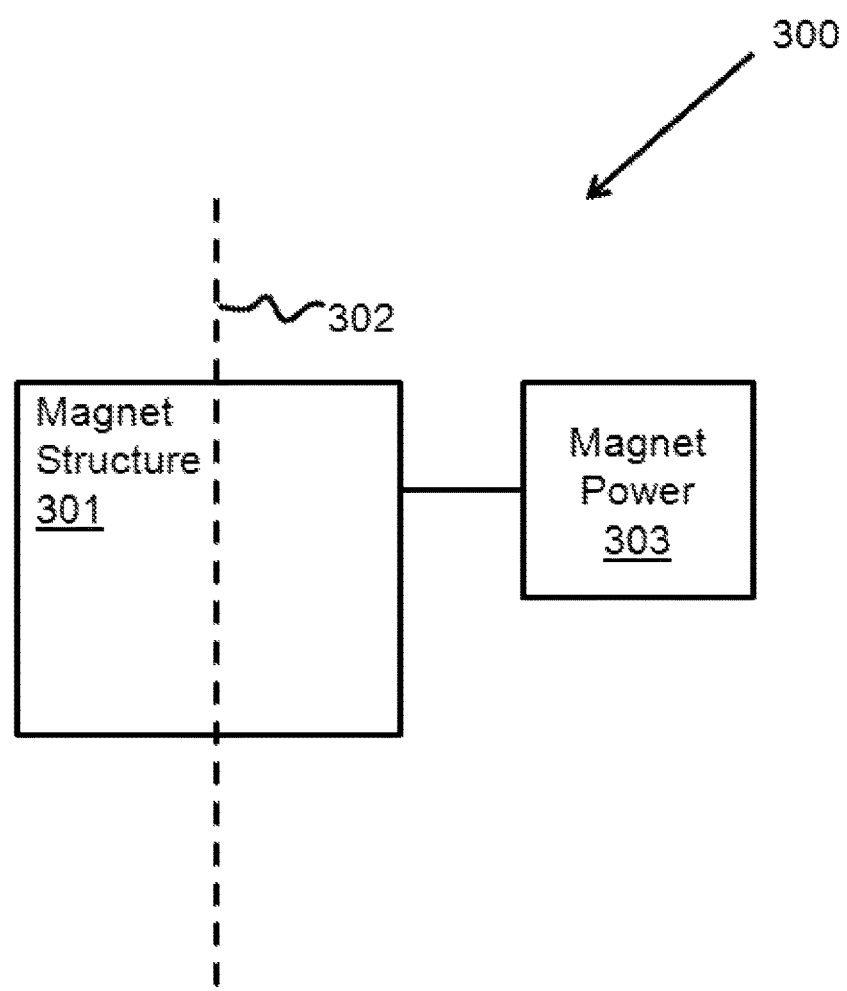
FIG. 3 illustrates a block diagram of a magnet structure and power source that can be used in accordance with the present invention.

A specific embodiment of the invention can be described with reference to FIG. 3. FIG. 3 illustrates scanning system 300 that may be used in place of scanning system 203 in FIG. 2. Scanning system 300 comprises a magnet structure 301 used to guide proton beam 302. Magnet structure 301 can alter its magnetic field to guide the magnet in 'x' and 'y' transversal directions. In specific embodiments of the invention, power is provided to magnet structure 301 through magnet power supply 303. In specific embodiments of the invention, magnet power supply 303 is controlled based on the energy of the proton beam and the target beam position at the target.

Figure 4:
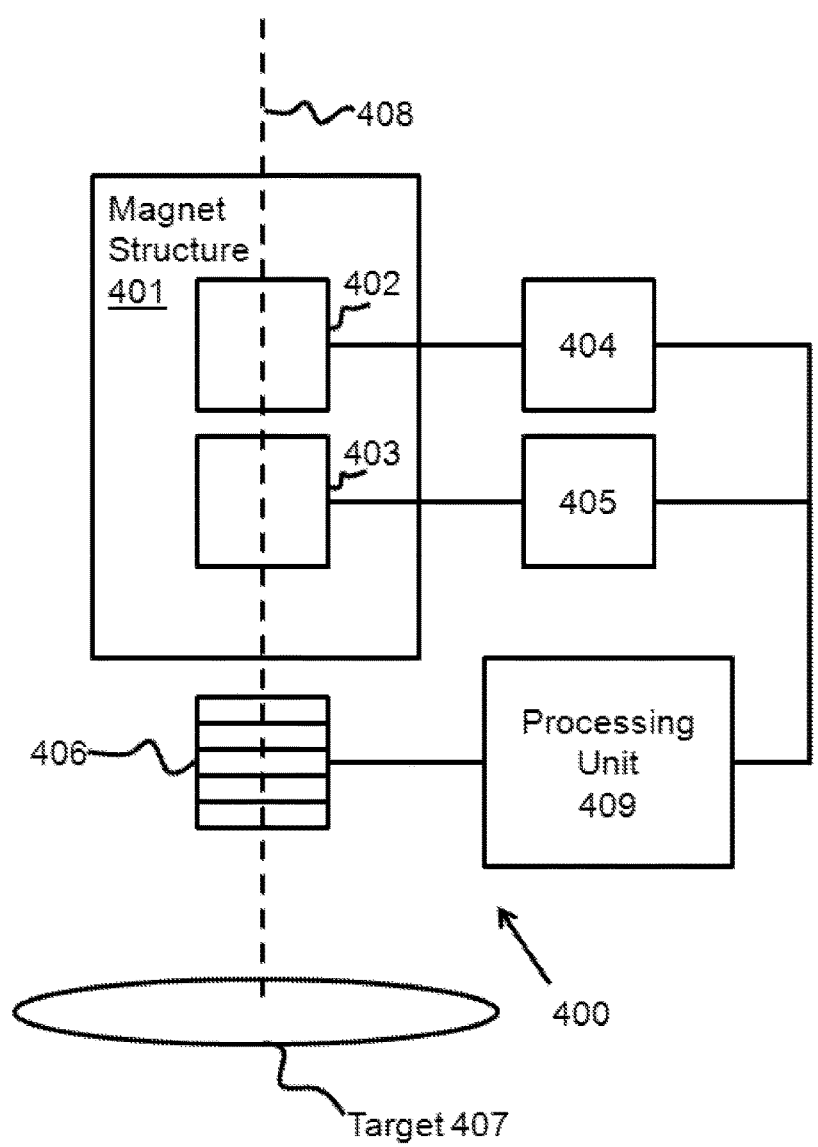
FIG. 4 illustrates block diagram of a scanning system that can be used in accordance with the present invention.

A specific embodiment of the invention can be described with reference to FIG. 4. FIG. 4 illustrates scanning system 400 that may be used in place of scanning system 203 in FIG. 2. Scanning system 400 comprises a magnet structure 401 used to guide the proton beam. In a first specific embodiments of the invention, magnet structure 401 comprises two scanning magnets as shown by y-directional magnet 402 and x-directional magnet 403. In specific embodiments of the invention, the magnets are powered by separate power supplies as shown by first magnet power supply 404 and second magnet power supply 405. Y-directional magnet 402 is capable of steering the proton beam in a transversal y-direction. X-directional magnet 403 is capable of steering the proton beam in a transversal x-direction.

In a second specific embodiments of the invention, magnet structure comprises one scanning magnet as shown by bi-directional magnet. In specific embodiments of the invention, the magnets comprises of two pairs of coils one for x direction and one for y direction. In specific embodiments of the invention, the coils of the magnets are powered by separate power supplies as shown by first magnet power supply and second magnet power supply. Bi-directional magnet is capable of steering the proton beam in a transversal y-direction and x-direction.

In specific embodiments of the invention, the scanning system will additionally comprise a transition ionization chamber such as transition ionization chamber 406. This transition ionization chamber is interspersed between magnet structure 401 and target 407 along proton beam path 408. Transition ionization chamber 406 is configured to measure the dose delivered to target 407. In specific embodiments of the invention, the dose delivered will be tracked for a particular location on target 407. In specific embodiments of the invention, the dose delivered will be tracked for the entire target 407. In specific embodiments of the invention, transition ionization chamber 406 will be a multi-strip ionization chamber comprising several Millimeter wide strips of conductive foil connected to electronic sensors. Multi-strip ionization chamber 406 is configured to measure an actual beam position on target 407 relative to the targeted location.

In specific embodiments of the invention, the data collected by transition ionization chamber 406 can be applied for various uses. As shown in FIG. 4, the collected data could be sent to real time processing unit 409. In specific embodiments of the invention, real time processing unit 409 will use information regarding the beam position, dose, treatment duration, and patient location data such as the depth of the tumor to direct magnet structure 401 so as to optimize the irradiation of target 407. For example, real time processing unit 409 could determine that the beam position does not match the desired location and could compensate for this deviation to more accurately match the beam position with the desired location. As another example, real time processing unit 409 could take in patient specific data in real time regarding the position of the tumor and adjust the location to which the proton beam is directed. In specific embodiments of the invention, real time processing unit 409 will deliver a first information to energy selection system 202. For example, this first information could be the depth of the tumor in a patient undergoing proton radiation therapy or the proton beam energy. In specific embodiments of the invention, real time processing unit 409 will deliver a second information to other components in scanning system 400. For example, this second information could be the beam position and target dose or data derived from beam position and target dose. Real time processing unit 409 therefore can allow for real time adjustment of the beam position, beam intensity, and Bragg peak depth based on patient specific information and actual measurement the proton beam's characteristics and location. In specific embodiments of the invention, the data collected by transition ionization chamber 406 could be output from the system for external use.

Figure 5:
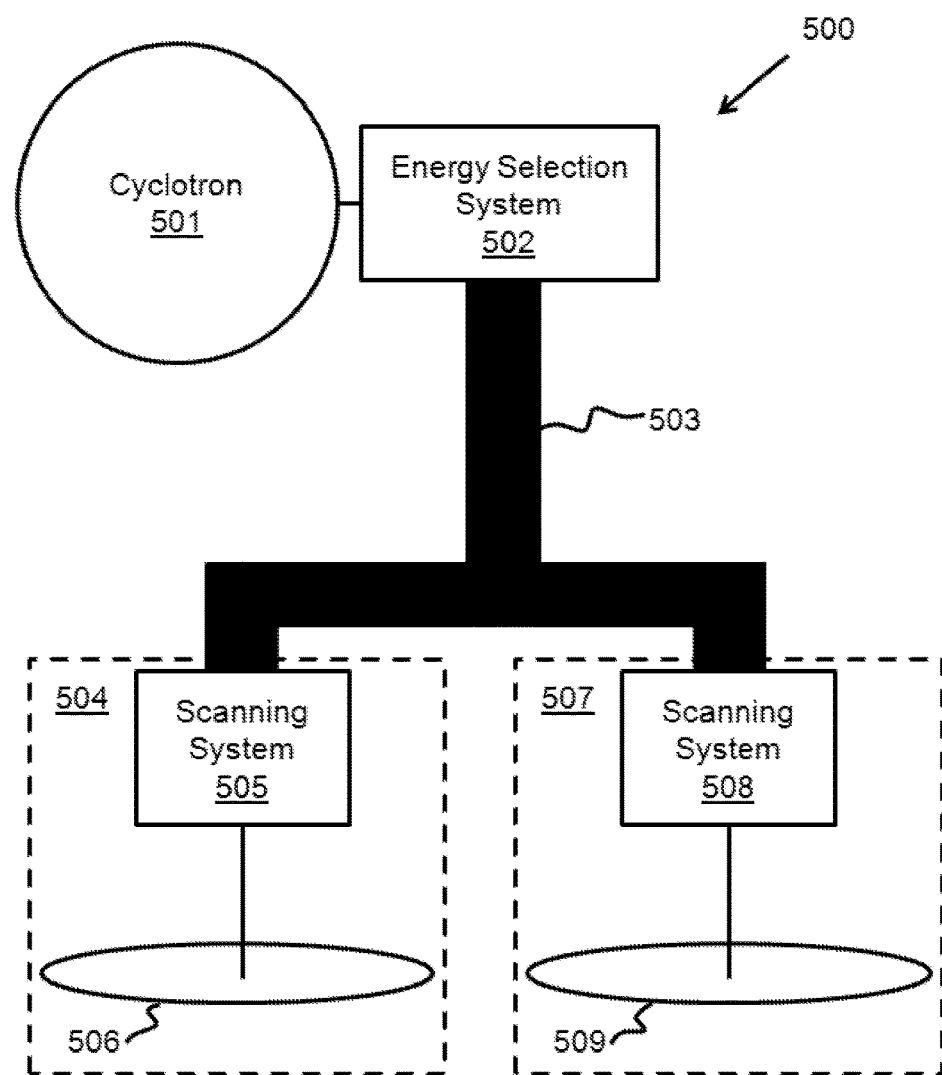
FIG. 5 illustrates a block diagram of a system for routing a proton beam to multiple locations that can be used in accordance with the present invention.

A specific embodiment of the invention can be described with reference to FIG. 5. FIG. 5 illustrates system 500. System 500 comprises a cyclotron 501 and an energy selection system 502. System 500 additionally comprises a beam transfer line 503. In specific embodiments of the invention, beam transfer line 503 will have multiple junctions having magnets or other devices for guiding the beam through various paths. In specific embodiments of the invention, certain paths may be shut-off while others remain open. Beam transfer line 503 leads to patient treatment room 504 having scanning system 505 and target 506. In specific embodiments of the invention, target 506 will be a tumor in a patient's body or some other target for proton beam irradiation. Beam transfer line 503 additionally leads to second patient treatment room 507 which may have second scanning system 508 and second target 509. In specific embodiments of the invention, scanning system 505 or scanning system 508 may have characteristics in accordance with those of scanning system 203.

In specific embodiments of the invention, energy selection system 502 may have characteristics in accordance with those of energy selection system 202. In specific embodiments of the invention, energy selection system 502 is able to receive patient specific information and proton beam related information from processing units in scanning system 505 and scanning system 508 as well as from other scanning systems to which beam transfer line 503 is connected. In specific embodiments of the invention, patient treatment room 504 and patient treatment room 507 are separate locations in the same facility which allows for the cost effective utilization of cyclotron 501.

Figure 6:
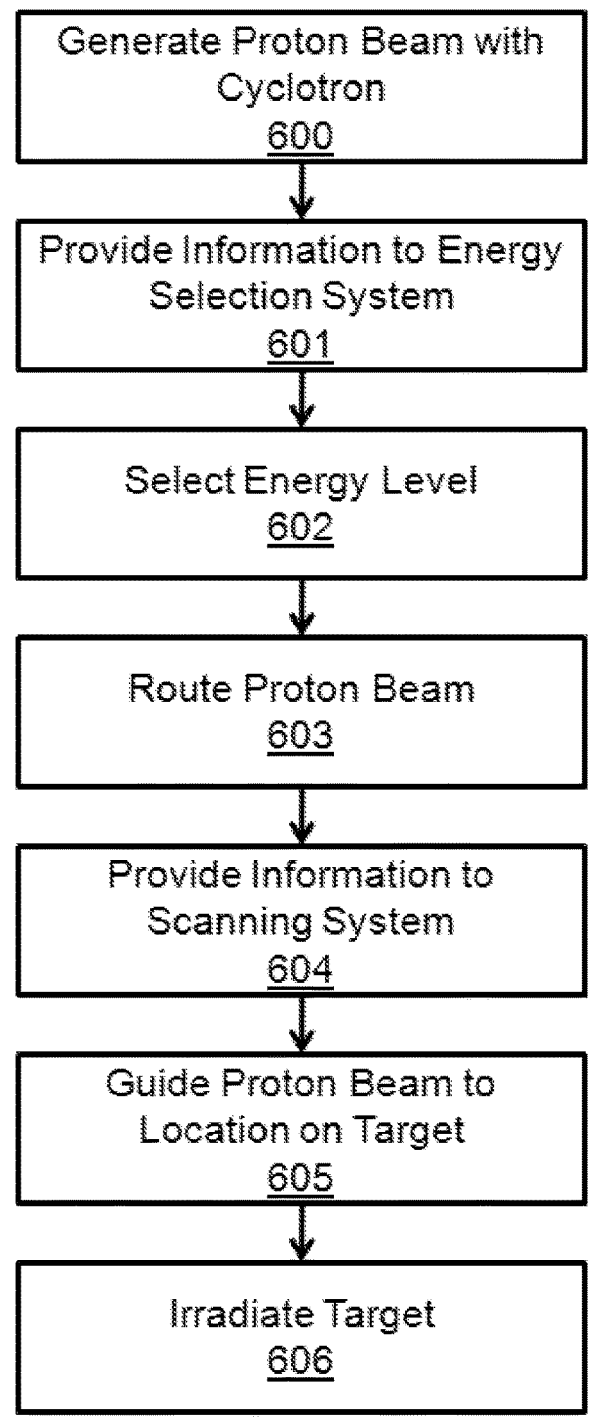
FIG. 6 illustrates a process flow chart of a method for irradiating a target that is in accordance with the present invention.

A specific embodiment of the invention can be described with reference to FIG. 6. FIG. 6 illustrates a method for irradiating a target. In step 600 a proton beam is generated using a cyclotron. The proton beam is comprised of a set of protons. The amount of protons per time is called beam intensity. In specific embodiments of the invention, the cyclotron is a superconducting cyclotron. In step 601 a first information is provided to an energy selection system. In specific embodiments of the invention, this first information is based on the depth to which the protons should be directed. In specific embodiments of the invention, this information is provided by a processing unit in a scanning system such as scanning system 203. In step 602 an energy level for the protons in the proton beam is selected using said energy selection system based on the first information. In step 603, the proton beam is routed from the cyclotron through a beam transfer line to a scanning system. In step 604, a second information is provided to the scanning system. In specific embodiments of the invention, the second information can comprise a pair of transversal coordinates (beam position) and target dose or derived from data from this.

In step 605, the proton beam is guided to a location on the target based on the second information. In step 606 the target is irradiated with protons. In specific embodiments of the invention, the method can be executed using an apparatus having characteristics in accordance with system 200.

In specific embodiments of the invention, the scanning system can measure data regarding the delivered proton beam which could then be used to adjust the proton beam in real time. In specific embodiments of the invention, the method will additionally comprise the step of measuring a dose delivered to the target at the desired location using a transition ionization chamber. In specific embodiments of the invention the transition ionization chamber will be a multi-strip ionization chamber. This method could also comprise the step of measuring a beam position on said target relative to the desired location for the beam using the transition ionization chamber. The ionization chamber is interspersed between the magnet structure and the target along the proton beam. The information obtained by the scanning system can be processed in real time. The second and first quanta of information can comprise this information.

In specific embodiments of the invention, the proton beam can be routed to multiple scanning systems. In specific embodiments of the invention, the method will additionally comprise the step of routing the proton beam form the cyclotron through the beam transfer line to a second scanning system. In specific embodiments of the invention, the target to which the beam is directed is a tumor. Routing the beam to multiple scanning systems that may be in multiple patient treatment rooms therefore allows a single cyclotron to be used to deliver proton therapy to multiple patients in a cost effective manner. In specific embodiments of the invention, the method can be executed using an apparatus having characteristics in accordance with system 500.

Although embodiments of the invention have been discussed primarily with respect to specific embodiments thereof, other variations are possible. Various configurations of the described system may be used in place of, or in addition to, the configurations presented herein. Those skilled in the art will appreciate that the foregoing description is by way of example only, and is not intended to limit the invention. Nothing in the disclosure should indicate that the invention is limited to radiation therapy as the targeted delivery of accelerated particles is useful in numerous other fields. Nothing in the disclosure should limit the scope of the invention to cancer treatment, irradiation of anatomical structures, or the use of any particular source material for the proton beam. Functions may be performed by hardware or software, as desired. In general, any diagrams presented are only intended to indicate one possible configuration, and many variations are possible. As used in the specification and in the appended claims the term "information" refers to a unit of information that can be in any form and size so long as it is comprises resolvable coherent information. As used in the specification and in the appended claims the term "transversal" is used to refer to movement in a plane that is normal to a vector defined by the nominal position of the proton beam. Those skilled in the art will also appreciate that methods and systems consistent with the present invention are suitable for use in a wide range of applications encompassing any related to proton acceleration or particle physics in general.

While the specification has been described in detail with respect to specific embodiments of the invention, it will be appreciated that those skilled in the art, upon attaining an understanding of the foregoing, may readily conceive of alterations to, variations of, and equivalents to these embodiments. These and other modifications and variations to the present invention may be practiced by those skilled in the art, without departing from the spirit and scope of the present invention, which is more particularly set forth in the appended claims.

What is claimed is:

1. A method for irradiating a target comprising the steps of:
   generating a proton beam using a cyclotron, said proton beam being comprised of a set of protons;
   providing a first information to an energy selection system, said first information comprising a depth of said target;
   selecting an energy level for said set of protons using said energy selection system based on said first information;
   routing said proton beam from said cyclotron through a beam transfer line to a scanning system, said scanning system comprises a magnet structure and an ionization chamber;
   providing a second information to said scanning system, said second information comprising a pair of transversal coordinates and target dose;
   guiding said proton beam using said magnet structure to a location on said target determined by said second information, said magnet structure comprises a bidirectional magnet with two pairs of coils one for x direction and one for y direction; and
   irradiating said target with said proton beam,
   wherein said magnet structure comprises a magnet power supply powering said magnet structure, said magnet power supply being controlled based on an energy of said proton beam and a beam position at a target of said proton beam.

2. The method of claim 1, wherein said magnet structure comprises a plurality of magnet sets, wherein said magnet power supply comprises a plurality of magnet power supplies, each magnet power supply of the plurality of magnet power supplies corresponding specifically to a magnet set of the plurality of magnet sets.

3. The method of claim 1, further comprising the step of measuring a beam position relative to said location and beam width during said irradiating step using multi strip ionization chamber.

4. The method of claim 1, further comprising the steps of:
   routing said proton beam from said cyclotron through said beam transfer line to a second scanning system;
   wherein said target is a tumor;
   wherein said scanning system is in a one or more treatment rooms each.

5. The method of claim 1, wherein said cyclotron is a superconducting cyclotron.

6. The method of claim 1, further comprising the steps of:
   measuring a dose delivered to said target during said irradiating step using a transition ionization chamber; and
   measuring a beam position relative to said location and beam width during said irradiating step using multi strip ionization chamber;
   wherein said transition ionization chamber is mounted between said magnet structure and said target along said proton beam.

7. The method of claim 6, further comprising the step of producing said first and second quanta of information in real time based on said beam position and said dose.

8. An apparatus for irradiating a target comprising:
   a cyclotron configured to generate a proton beam, said proton beam comprising a set of protons;
   an energy selection system configured to select an energy level for said set of protons from a set of three or more energy levels;
   a scanning system configured to guide said proton beam to a location on said target using a magnet structure, said scanning system comprises said magnet structure and an ionization chamber, said magnet structure comprises a bidirectional magnet with two pairs of coils one for x direction and one for y direction;
   a beam transfer line configured to route said proton beam from said cyclotron to said scanning system; and
   a magnet power supply powering said magnet structure, said magnet power supply being controlled based on an energy of said proton beam and a beam position at a target of said proton beam, wherein said energy selection system selects said energy level based on a first information;
wherein said scanning system guides said proton beam to said location based on a second information.

9. The apparatus from claim 8, wherein said magnet structure comprises a plurality of magnet sets, wherein said magnet power supply comprises a plurality of magnet power supplies, each magnet power supply of the plurality of magnet power supplies corresponding specifically to a magnet set of the plurality of magnet sets.

10. The apparatus from claim 8, further comprising:
a second scanning system located in a second patient treatment room, said second scanning system configured to guide said proton beam using a second magnet structure;
wherein said scanning system is located in a patient treatment room.

11. The apparatus from claim 8, further comprising a transition ionization chamber interspersed between said magnet structure and said target along a path of said proton beam, said transition ionization chamber being configured to measure a dose delivered to said target at said location.

12. The apparatus from claim 11, further comprising a multi-strip ionization chamber interspersed between said magnet structure and said target along said path of said proton beam, said multi-strip ionization chamber being configured to measure a beam position relative to said location.

13. The apparatus from claim 12, wherein:
said first information is based on a depth of said target; and
said second information is based on said beam position and said dose.

14. A system for irradiating a tumor of a patient comprising:
a superconducting cyclotron configured to generate a proton beam;
an energy selection system configured to select an energy level for said proton beam based on a depth of said tumor;
a scanning system configured to guide said proton beam using a magnet structure to a location on said tumor, said scanning system comprises said magnet structure and an ionization chamber, said magnet structure comprises a bidirectional magnet with two pairs of coils one for x direction and one for y direction; and
a magnet power supply powering said magnet structure, said magnet power supply being controlled based on an energy of said proton beam and a beam position at a target of said proton beam.

15. The system from claim 14, wherein said magnet structure comprises a plurality of magnet sets, wherein said magnet power supply comprises a plurality of magnet power supplies, each magnet power supply of the plurality of magnet power supplies corresponding specifically to a magnet set of the plurality of magnet sets.

16. The system from claim 14, further comprising a beam transfer line configured to route said proton beam from said superconducting cyclotron to said scanning system.

17. The system from claim 14, further comprising:
a second scanning system located in a second patient treatment room, said second scanning system configured to guide said proton beam using a second magnet structure;
wherein said scanning system is located in a patient treatment room; and
wherein said second patient treatment room is separate from said patient treatment room.

18. The system from claim 14, further comprising a transition ionization chamber mounted between said magnet structure and said tumor along a path of said proton beam, said transition ionization chamber being configured to measure a dose delivered to said tumor.

19. The system from claim 18, further comprising a multi-strip ionization chamber mounted between said magnet and said target along said proton beam, said multi-strip ionization chamber being configured to measure a beam position relative to said location.

20. The system from claim 19, wherein said scanning system alters said beam position and depth of said tumor in real time based on said dose.

* * * * *